(12) United States Patent
Takada et al.

(10) Patent No.: US 9,102,602 B2
(45) Date of Patent: Aug. 11, 2015

(54) METHOD FOR PRODUCING ISOTHIOCYANATE COMPOUND

(75) Inventors: Junko Takada, Funabashi (JP); Shunsuke Iwamoto, Funabashi (JP); Satoshi Nakano, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 13/990,312

(22) PCT Filed: Nov. 29, 2010

(86) PCT No.: PCT/JP2010/071294
§ 371 (c)(1),
(2), (4) Date: May 29, 2013

(87) PCT Pub. No.: WO2012/073314
PCT Pub. Date: Jun. 7, 2012

(65) Prior Publication Data
US 2013/0245305 A1    Sep. 19, 2013

(51) Int. Cl.
*C07C 331/28*    (2006.01)

(52) U.S. Cl.
CPC ................ *C07C 331/28* (2013.01)

(58) Field of Classification Search
CPC .................................................. C07C 331/28
See application file for complete search history.

(56) References Cited

U.S. PATENT DOCUMENTS

| | | | |
|---|---|---|---|
| 4,228,165 A | 10/1980 | Ogata et al. | |
| 4,248,869 A | 2/1981 | Ogata et al. | |
| 5,310,916 A | 5/1994 | Jacobson et al. | |
| 6,720,346 B2 * | 4/2004 | Chu et al. | 514/370 |
| 7,435,823 B2 * | 10/2008 | Potashman et al. | 546/153 |
| 7,470,712 B2 * | 12/2008 | Herpin et al. | 514/338 |

FOREIGN PATENT DOCUMENTS

| | | |
|---|---|---|
| JP | 54 55550 | 5/1979 |
| JP | 2000 351762 | 12/2000 |
| JP | 2002 524524 | 8/2002 |
| JP | 2002 539184 | 11/2002 |
| JP | 2003 176265 | 6/2003 |
| JP | 2005 521631 | 7/2005 |
| WO | 95 09013 | 4/1995 |
| WO | WO 2006/047354 A1 | 5/2006 |
| WO | 2008 082692 | 7/2008 |
| WO | 2009 107796 | 9/2009 |

OTHER PUBLICATIONS

Nishimura et al. (Angew. Chem. Int. Ed. 2008, 47, 6077-6079 and supporting information p. 1-12).*
J. Ian Grayson (Organic Process Research and Development (1997), vol. 1 (3); pp. 240-1246).*
Gauthier et al. (Bioorganic & Medicinal Chemistry 14 (2006) 918-927).*
Eidelman, O. et al., "Macromolecular Conjugates of Transport Inhibitors: New Tools for Probing Topography of Anion Transport Proteins", American Journal of Physiology, vol. 260, No. 5, Part 1, pp. C1094-C1103, (May 1991).
McKee, R. L. et al., "p-Substituted Phenyl Isothiocyanates and Some Related Thioureas", J. Am. Chem. Soc., vol. 68. pp. 2506-2507, (1946).
Kricheldorf, H.R., "Methoden zur Herstellung von Isothiocyanatocarbonsaeure-trimethylsilylestern", Liebigs Ann. Chem, vol. 748, pp. 101-108, (1971).
Boi, L.V. et al., "Thiocarbamoylation of Amine-containing Compounds 1. The Reaction of Tetramethylthiuram Disulfide with 3-amino-4-methylbenzoic acid", Russian Chemical Bulletin, vol. 48, No. 4. pages 739-742, (1999).
International Search Report issued Feb. 22, 2011 in PCT/JP10/071294 filed Nov. 29, 2010.
Japanese Office Action Issued Nov. 14, 2012 in JP Patent Application No. 2009 203114 (with English translation).
Henrik Munch, et al., "A new efficient synthesis of isothiocyanates from amines using di-tert-butyl dicarbonate", Tetrahedron Letters, 49, 2008, 3117-3119.

* cited by examiner

*Primary Examiner* — Valerie Rodriguez-Garcia
(74) *Attorney, Agent, or Firm* — Oblon, McClelland, Maier & Neustadt, L.L.P.

(57) ABSTRACT

The object of the present invention is to provide a novel method for producing an isothiocyanate compound having a carboxyl group(s) by a reaction of the corresponding amino compound having a carboxyl group(s), thiocarbonyldiimidazole and a base, in one step with high purity. An amino compound having a carboxyl group(s) is reacted with thiocarbonyldiimidazole in a solvent in the presence of a base to obtain an isothiocyanate compound having a carboxyl group(s).

9 Claims, No Drawings

METHOD FOR PRODUCING ISOTHIOCYANATE COMPOUND

CROSS REFERENCE TO RELATED APPLICATIONS

The present application is a 35 U.S.C. §371 national stage patent application of International patent application PCT/JP2010/071294, filed on Nov. 29, 2010, published as WO/2012/073314 on Jun. 7, 2012, the text of which is incorporated by reference.

TECHNICAL FIELD

The present invention relates to a method for producing an isothiocyanate compound having a carboxyl group(s) from the corresponding amino compound having a carboxyl group(s).

BACKGROUND ART

An isothiocyanate group is a very useful functional group in synthetic organic chemistry since its reactivity is high and it can be led to various chemical structures. And, a carboxyl group is a useful functional group in the field of organic materials, drugs or agricultural chemicals because of its characteristic acidity and hydrogen bonding ability. Accordingly, an isothiocyanate compound having a carboxyl group(s), which has such two functional groups in one molecule, can be said to be a very useful compound as a product or a synthetic intermediate in the field of organic materials, drugs or agricultural chemicals. As an example, it is known that 3,5-diisocyanatobenzoic acid is useful as a starting material for the synthesis of a metal-binding polypeptide (e.g. Patent Document 1).

As a method for producing an isothiocyanate compound having a carboxyl group(s) from the corresponding amino compound having a carboxyl group(s), a method of using thiophosgene (e.g. Non-Patent Document 1) and a method of using chlorothionoformic acid phenyl ester (e.g. Non-Patent Document 2) have been reported, however, they have a problem that these compounds have a very strong toxicity and bad odor. Further, a method of using tetramethylthiuram disulfide has been reported (e.g. Non-Patent Document 3), but it has a problem that isolation of reaction intermediate is necessary, whereby the operation is cumbersome; the reaction condition is severe such that heating is carried out at a high temperature in the presence of acid; and tetramethylthiuram disulfide to be used is expensive. Therefore, it has been desired to develop a novel method for producing an isothiocyanate compound having a carboxyl group(s) in a high yield and with high purity without using such reagents, which is useful also as an industrial production method.

PRIOR ART DOCUMENTS

Patent Document

Patent Document 1: WO95/09013

Non-Patent Documents

Non-Patent Document 1: J. Am. Chem. Soc. (1946), 68, 2506
Non-Patent Document 2: Justus Liebigs Annalen der Chemie, (1971), 748, 101
Non-Patent Document 3: Russ. Chem. Bull. (1999), 48, 739

DISCLOSURE OF INVENTION

Technical Problem

It is an object of the present invention to provide a novel method capable of producing an isothiocyanate compound having a carboxyl group(s) from the corresponding amino compound having a carboxyl group(s) using a safe reagent in a high yield and with high purity, which is useful as an industrial production method.

Solution to Problem

The present inventors have conducted an extensive study to solve the above problems and as a result, they have found a novel method for producing an isothiocyanate compound having a carboxyl group(s) by reacting the corresponding amino compound having a carboxyl group(s) and thiocarbonyldiimidazole, in a high yield and with high purity and thus accomplished the present invention.

That is, the present invention provides the following.

(1) A method for producing an isothiocyanate compound which has a carboxyl group(s) and is represented by the formula (2):

$$(SCN)_m\text{-A-B-}(CO_2H)_n \qquad (2)$$

wherein m, n, A and B are, respectively, as defined in the formula (1), said method comprising reacting an amino compound which has a carboxyl group(s) and is represented by the formula (1):

$$(H_2N)_m\text{-A-B-}(CO_2H)_n \qquad (1)$$

[wherein each of m and n which are independent of each other, is an integer of 1 or 2, A is a $C_{6-14}$ aromatic hydrocarbon group or a $C_{1-12}$ saturated hydrocarbon group (said $C_{6-14}$ aromatic hydrocarbon group and $C_{1-12}$ saturated hydrocarbon group are unsubstituted or substituted with a halogen atom(s), a nitro group(s), a cyano group(s), a $C_{1-6}$ alkyl group(s), a hydroxy group(s), a protected hydroxy group(s), a $C_{1-6}$ alkoxy group(s), a di $C_{1-6}$ alkylamino group(s), a protected amino group(s), a protected mono $C_{1-6}$ alkylamino group(s), a $C_{1-6}$ alkylcarbonyl group(s) or a $C_{1-6}$ alkoxycarbonyl group(s), and the methylene group(s) in said $C_{1-12}$ saturated hydrocarbon group may be replaced by an oxygen atom(s), a nitrogen atom(s) substituted with a $C_{1-6}$ alkyl group, or a protected nitrogen atom(s)), and B is a single bond, a $C_{6-14}$ aromatic hydrocarbon group or a $C_{1-12}$ saturated hydrocarbon group (said $C_{6-14}$ aromatic hydrocarbon group and $C_{1-12}$ saturated hydrocarbon group are unsubstituted or substituted with a halogen atom(s), a nitro group(s), a cyano group(s), a $C_{1-6}$ alkyl group(s), a hydroxy group(s), a protected hydroxy group(s), a $C_{1-6}$ alkoxy group(s), a di $C_{1-6}$ alkylamino group(s), a protected amino group(s), a protected mono $C_{1-6}$ alkylamino group(s), a $C_{1-6}$ alkylcarbonyl group(s) or a $C_{1-6}$ alkoxycarbonyl group(s), and the methylene group(s) in said $C_{1-12}$ saturated hydrocarbon group may be replaced by an oxygen atom(s), a nitrogen atom(s) substituted with a $C_{1-6}$ alkyl group, or a protected nitrogen atom(s))], with thiocarbonyldiimidazole in a solvent in the presence of a base.

(2) The method according to (1), wherein A is a $C_{6-14}$ aromatic hydrocarbon group (said $C_{6-14}$ aromatic hydrocarbon group is unsubstituted or substituted with a halogen atom(s), a nitro group(s), a cyano group(s), a $C_{1-6}$ alkyl group(s), a protected hydroxy group(s), a $C_{1-6}$ alkoxy group(s), a di $C_{1-6}$ alkylamino group(s), a protected amino group(s), a protected mono $C_{1-6}$ alkylamino group(s), a $C_{1-6}$ alkylcarbonyl group(s) or a $C_{1-6}$ alkoxycarbonyl group(s)), and B is a single bond.

(3) The method according to (2), wherein A is a $C_{6-14}$ aromatic hydrocarbon group (said $C_{6-14}$ aromatic hydrocarbon group is unsubstituted or substituted with a halogen atom(s) or a nitro group(s)).
(4) The method according to (3), wherein m is 1, and n is 1.
(5) The method according to (4), wherein A is a phenylene group (said phenylene group is unsubstituted or substituted with a halogen atom(s) or a nitro group(s)).
(6) The method according to any one of (1) to (5), wherein the base is a tertiary amine.
(7) The method according to (6), wherein the base is a tri $C_{1-6}$ alkyl amine.
(8) The method according to (7), wherein the base is triethylamine.
(9) The method according to any one of (1) to (8), wherein the solvent is a halogenated hydrocarbon.
(10) The method according to (9), wherein the solvent is methylene chloride.
(11) The method according to any one of (1) to (10), wherein the amino compound which has a carboxyl group(s) is reacted with thiocarbonyldiimidazole in the solvent in the presence of the based, followed by a treatment with an acidic aqueous solution.
(12) The method according to (11), wherein the acidic aqueous solution is hydrochloric acid.
(13) The method according to (12), wherein after the treatment with hydrochloric acid, without a liquid separation operation, a filtration operation is carried out.
(14) The method according to (13), wherein after the treatment with hydrochloric acid, without a liquid separation operation, a poor solvent is added and then a filtration operation is carried out.
(15) The method according to (14), wherein the poor solvent is water or a $C_{5-8}$ alkane.

Advantageous Effects of Invention

According to the present invention, it is possible to provide a novel method whereby without using strongly toxic thiophosgene and chlorothioformic acid ethyl ester or expensive tetramethylthiuram disulfide, an isothiocyanate compound can be produced from the corresponding amino compound having a carboxyl group(s) safely, inexpensively, simply in a high yield and with high purity under mild conditions.

DESCRIPTION OF EMBODIMENTS

Now, the present invention will be described in further detail.

In the present invention, "n" means normal, "i" iso, "s" or "sec" secondary, "t" or "tert" tertiary, "c" cyclo, "o" ortho, "m" meta, and "p" para.

The $C_{1-6}$ alkyl group represents a linear, branched or cyclic alkyl group having from 1 to 6 carbon atoms and may, for example, be a methyl group, an ethyl group, a n-propyl group, a n-butyl group, a n-pentyl group, a n-hexyl group, an i-propyl group, an i-butyl group, a t-butyl group, a s-butyl group, an i-pentyl group, a neopentyl group, a t-pentyl group, a c-propyl group, a c-butyl group, a c-pentyl group or a c-hexyl group.

The $C_{1-6}$ alkoxy group represents a linear, branched or cyclic alkoxy group having from 1 to 6 carbon atoms and may, for example, be a methoxy group, an ethoxy group, a n-propoxy group, an i-propoxy group, a n-butoxy group, an i-butoxy group, a s-butoxy group, a t-butoxy group, a n-pentyloxy group, an i-pentyloxy group, a n-hexyloxy group, a c-butyloxy group, a c-pentyloxy group or a c-hexyloxy group.

The $C_{1-6}$ alkylcarbonyl group represents a carbonyl group substituted with a $C_{1-6}$ alkyl group and may, for example, be a methylcarbonyl group, an ethylcarbonyl group, a n-propylcarbonyl group, a n-butylcarbonyl group, a n-pentylcarbonyl group, a n-hexylcarbonyl group, an i-propylcarbonyl group, an i-butylcarbonyl group, a t-butylcarbonyl group, a s-butylcarbonyl group, an i-pentylcarbonyl group, a neopentylcarbonyl group, a t-pentylcarbonyl group, a c-propylcarbonyl group, a c-butylcarbonyl group, a c-pentylcarbonyl group or a c-hexylcarbonyl group.

The mono $C_{1-6}$ alkylamino group represents an amino group substituted with one $C_{1-6}$ alkyl group and may, for example, be an N-methylamino group, an N-ethylamino group, an N-n-propylamino group, an N-i-propylamino group, an N-n-butylamino group, an N-i-butylamino group, an N-s-butylamino group, an N-t-butylamino group, an N-n-pentylamino group, an N-i-pentylamino group, an N-neopentylamino group, an N-t-pentylamino group, an N-n-hexylamino group, an N-c-propylamino group, an N-c-butylamino group, an N-c-pentylamino group, an N-c-hexylamino group, an N-c-propylmethylamino group, an N-c-butylmethylamino group or an N-c-pentylmethylamino group.

The di $C_{1-6}$ alkylamino group represents an amino group substituted with the same or different two $C_{1-6}$ alkyl groups and may, for example, be an N,N-dimethylamino group, an N,N-diethylamino group, an N,N-di-n-propylamino group, an N,N-di-i-propylamino group, an N-methyl-N-ethylamino group, an N-methyl-N-n-propylamino group, an N-methyl-N-i-propylamino group, an N-ethyl-N-n-propylamino group, an N-ethyl-N-i-propylamino group or an N-n-propyl-N-i-propylamino group.

The $C_{1-6}$ alkoxycarbonyl group represents a carbonyl group substituted with a $C_{1-6}$ alkoxy group and may, for example, be a methoxycarbonyl group, an ethoxycarbonyl group, a n-propoxycarbonyl group, an i-propoxycarbonyl group, a n-butoxycarbonyl group, an i-butoxycarbonyl group, a s-butoxycarbonyl group, a t-butoxycarbonyl group, a n-pentyloxycarbonyl group, an i-pentyloxycarbonyl group, a n-hexyloxycarbonyl group, a c-butyloxycarbonyl group, a c-pentyloxycarbonyl group or a c-hexyloxycarbonyl group.

The $C_{1-12}$ saturated hydrocarbon group represents a bivalent or trivalent group derived from a saturated hydrocarbon of a linear, branched or cyclic alkyl group having from 1 to 12 carbon atoms and may, for example, be a bivalent or trivalent group derived from e.g. methane, ethane, n-propane, n-butane, n-pentane, n-hexane, n-heptane, n-octane, i-propane, i-butane, t-butane, s-butane, i-pentane, neopentane, t-pentane, c-propane, c-butane, c-pentane, c-hexane, c-heptane, c-hexylmethane or c-hexylethane.

The $C_{1-12}$ saturated hydrocarbon group in A and B in the formula (1) may have a substituent as defined above. For example, the $C_{1-12}$ saturated hydrocarbon group for A when m is 1, or the $C_{1-12}$ saturated hydrocarbon group for B when n is 1, is a linear, branched or cyclic alkylene (alkane-diyl) group having from 1 to 12 carbon atoms, and such an alkylene group is unsubstituted or substituted as defined in the definition of A or B. Further, the $C_{1-12}$ saturated hydrocarbon group for A when m is 2, or the $C_{1-12}$ saturated hydrocarbon group for B when n is 2, is a linear, branched or cyclic alkane-triyl group having from 1 to 12 carbon atoms, and such an alkane-triyl group is unsubstituted or substituted as defined in the definition of A or B.

The $C_{1-12}$ saturated hydrocarbon group in the present invention is preferably a $C_{1-6}$ saturated hydrocarbon group in which the number of carbon atoms in the $C_{1-12}$ saturated hydrocarbon group is limited to from 1 to 6, and is more preferably a methylene group or an ethylene group.

The $C_{6-14}$ aromatic hydrocarbon group is a bivalent or trivalent group derived from an aromatic hydrocarbon having from 6 to 14 carbon atoms and may, for example, be a bivalent or trivalent group derived from benzene, naphthalene, biphenyl or anthracene.

The $C_{6-14}$ aromatic hydrocarbon group in A and B in the formula (1), may be substituted as defined in the definition of A or B. For example, the $C_{6-14}$ aromatic hydrocarbon group for A when m is 1, or the $C_{6-14}$ aromatic hydrocarbon group for B when n is 1, is an arylene (aryl-diyl) group having from 6 to 14 carbon atoms, and such arylene group is unsubstituted or substituted as defined in the definition of A or B. Further, the $C_{6-14}$ aromatic hydrocarbon group for A when m is 2, or the $C_{6-14}$ aromatic hydrocarbon group for B when n is 2, is an aryl-triyl group having from 6 to 14 carbon atoms, and such an aryl-triyl group is unsubstituted or substituted as defined in the definition of A or B.

The $C_{6-14}$ aromatic hydrocarbon group in the present invention is preferably a $C_{6-10}$ saturated hydrocarbon group in which the number of carbon atoms in the $C_{6-14}$ aromatic hydrocarbon group is limited to from 6 to 10, and is more preferably a phenylene group or a naphthylene group, and is further preferably a phenylene group.

The protecting group in the protected hydroxy group may be any protecting group so long as it is effective as a protecting group for a hydroxy group, and for example, protecting groups disclosed in Greene's Protective Groups in Organic Synthesis (4th ed.), John Wiley, 2007, pp. 24-299 may be mentioned.

The protecting groups in the protected amino group, the protected mono $C_{1-6}$ alkylamino group and the protected nitrogen atom may be any protecting groups so long as they are effective as protecting groups for a nitrogen atom, and for example, protecting groups disclosed in e.g. Greene's Protective Groups in Organic Synthesis (4th ed.), John Wiley, 2007, pp. 706-872 may be mentioned.

Now, the preferred structure in the formula (1) in the present invention is shown below.

m is preferably 1.
n is preferably 1.
B is preferably a single bond or a $C_{1-6}$ alkylene group, more preferably a single bond.

The $C_{6-14}$ aromatic hydrocarbon group in A may be substituted with a functional group(s) which will not directly react with the base to be used and thiocarbonyldiimidazole. Such a functional group may be a substituent having no acidic proton or a substituent having an acidity lower than that of a carboxyl group such as a hydroxy group. Specific examples preferably include a halogen atom, a nitro group, a cyano group, a $C_{1-6}$ alkyl group, a hydroxy group, a protected hydroxy group, a $C_{1-6}$ alkoxy group, a di $C_{1-6}$ alkylamino group, a protected amino group, a protected mono $C_{1-6}$ alkylamino group, a $C_{1-6}$ alkylcarbonyl group and a $C_{1-6}$ alkoxycarbonyl group. More preferred is a halogen atom, a nitro group, a $C_{1-3}$ alkyl group or a $C_{1-3}$ alkoxy group, and further preferred is a chlorine atom or a nitro group.

Preferred specific examples of the base include organic amines such as diethylamine, triethylamine, diisopropylethylamine, tri-n-propylamine, tri-n-butylamine, DBN (1,5-diazabicyclo[4.3.0]-5-nonene), DBU (1,8-diazabicyclo[5.4.0]-7-undecene), N-methylmorpholine and N,N-dimethylaniline and inorganic bases such as sodium hydroxide, potassium carbonate and sodium hydrogencarbonate. More preferred is an organic amine, particularly a tertiary amine, and further preferred is a tri $C_{1-6}$ alkylamine such as triethylamine, diisopropylethylamine, tri-n-propylamine or tri-n-butylamine, and particularly preferred is triethylamine.

In the production method of the present invention, the amino compound having a carboxyl group(s) and thiocarbonyldiimidazole are reacted in a solvent in the presence of a base, and the order of addition of such raw materials and the base into the solvent is not particularly limited so long as it has not affects the reaction. Preferred is a method of adding the amino compound having a carboxyl group(s) into a solution of the base and thiocarbonyldiimidazole, a method of adding a solution of the base and thiocarbonyldiimidazole to a solution of the amino compound having a carboxyl group(s), or a method of adding the base and thiocarbonyldiimidazole to a solution of the amino compound having a carboxyl group(s). Particularly, since thiocarbonyldiimidazole is a solid, the former two methods are more preferred as an industrial production method.

In the production method of the present invention, the reaction time is preferably from one minute to 4 hours, more preferably from 5 minutes to 2 hours, further preferably from 10 minutes to 1 hour.

In the production method of the present invention, it is preferred that after completion of the reaction, a treatment with an acid is carried out to obtain the desired product. The amount of use of the acid is preferably at least (the number of moles of thiocarbonyldiimidazole×2.0+the number of moles of the base) per 1 mol of the amino compound having a carboxyl group(s). The type of the acid is not particularly limited so long as it can be used for the treatment, and preferred is an acid having an acidity higher than that of the desired isothiocyanate compound having a carboxyl group(s). Such an acid is preferably a strong acid having a pKa value of at most 0, more preferably hydrochloric acid which is easily available and is easily handled from an industrial viewpoint. Hydrochloric acid is preferably hydrochloric acid having a concentration of at least 4 M, more preferably concentrated hydrochloric acid.

In the production method of the present invention, as the treatment after completion of the reaction, it is preferred to separate the base remaining after the reaction and imidazole formed after the reaction from the desired isothiocyanate compound having a carboxyl group(s). The method may be a solvent treatment method of adding, to the reaction mixture after the reaction, a solvent in which the base and imidazole are dissolved but the desired product is not dissolved, and as a preferred specific example of such a solvent, water may be mentioned. As a treatment method of carrying out the above-described acid treatment and the solvent treatment all at once, preferred is a method of adding an acidic aqueous solution after completion of the reaction so that the base and imidazole are dissolved in the acidic aqueous solution and separated. As the procedure of adding the acidic aqueous solution, the acidic aqueous solution may be added to the reaction system, or the reaction mixture may be added to the acidic aqueous solution, but more preferred is the procedure of adding the reaction mixture to the acidic aqueous solution. Further, the acidic aqueous solution is preferably hydrochloric acid.

Further, as an industrial production method, it is desirable to obtain the desired product by a treatment method as simple as possible, and as one of such methods, preferred is a method of directly crystallizing the desired product from the reaction mixture and obtaining the desired product only by a filtration operation. As a means to crystallize the desired product, it is preferred to cool the reaction mixture or to use a poor solvent. The poor solvent is preferably water, a $C_{5-8}$ alkane, diethyl ether or diisopropyl ether, more preferably a $C_{5-8}$ alkane, further preferably n-hexane or n-heptane. The amount of use of the poor solvent is preferably from 1 to 50 times by volume, more preferably from 7 to 10 times by volume per mass 1 of the amino compound having a carboxyl group(s).

Here, as times by volume, the proportion of 1 mL of a liquid to 1 g of a solid is 1 time.

Further, the $C_{5-8}$ alkane represents an alkane having from 5 to 8 carbon atoms, the alkane may be linear or branched or a cycloalkane, and specific examples thereof include n-pentane, n-hexane, n-heptane and c-hexane.

Further, as a method to achieve separation of the base and imidazole with the acidic aqueous solution and direct crystallization of the desired product from the reaction mixture to obtain the desired product only by a filtration operation at the same time, it is preferred that a water-insoluble organic solvent is used as the reaction solvent and the acidic aqueous solution is added in the treatment after the reaction and then or at the same time the reaction mixture is cooled or the poor solvent is used for crystallization, followed by filtration in a suspended state of the desired crystals, the reaction solvent, the acidic aqueous solution and/or the poor solvent.

As a particularly preferred procedure, the reaction mixture after completion of the reaction is dropped to a mixture of the acidic aqueous solution and the poor solvent for crystallization, and the desired product is obtained by filtration.

The reaction time, the stirring time after the treatment with an acid, and the like, vary depending upon the reaction temperature, and the type and the amount of use of the material compounds, and are properly changed depending upon the respective conditions, however, it is necessary to satisfy the conditions such as the purification effect, the desired product recovery effect and the operation efficiency in a well balanced manner while e.g. decomposition of the desired product by an acid is suppressed.

The stirring time after the treatment with an acid is more preferably within a range of from 5 minutes to 3 hours, further preferably from 1 to 3 hours.

The reaction solvent to be used for the production method of the present invention is not particularly limited so long as it is stable under the reaction conditions and is inert so as not to inhibit the reaction. The reaction solvent is preferably a water-insoluble organic solvent, more preferably a halogenated hydrocarbon, particularly preferably methylene chloride. The amount of use of the reaction solvent is preferably from 1 to 50 times by volume, more preferably from 5 to 15 times by volume per mass 1 of the amine compound having a carboxyl group(s).

The production method of the present invention may be carried out at a reaction temperature from a temperature at which the reaction solvent is not frozen to the boiling point of the solvent. The reaction temperature when the amino compound having a carboxyl group(s), thiocarbonyldiimidazole and the base are mixed is preferably from −10 to 40° C., more preferably from −10 to 10° C. The temperature when the substrate is reacted is preferably from −10 to 40° C., more preferably from −10 to 10° C., further preferably from 0 to 5° C. The temperature when the treatment with an acid is carried out is preferably from −10 to 40° C., more preferably from 0 to 30° C., further preferably from 25 to 30° C. The temperature when stirring is carried out after the treatment with an acid is preferably from −10 to 30° C., more preferably from 0 to 30° C., further preferably from 25 to 30° C.

The amount of use of thiocarbonyldiimidazole is properly (the number of amino group(s) in one molecule of the material×1.0 to the number of amino group(s) in one molecule of the material×10.0) mols, preferably (the number of amino group(s) in one molecule of the material×1.2 to the number of amino group(s) in one molecule of the material×1.5) mols per 1 mol of the amino compound having a carboxyl group(s).

The amount of use of the base is properly [(the number of carboxyl group(s) in one molecule of the material×1.0) to (the number of carboxyl group(s) in one molecule of the material×5.0)] mols, preferably [(the number of carboxyl group(s) in one molecule of the material×1.1) to (the number of carboxyl group(s) in one molecule of the material+the number of amino group(s) in one molecule of the material×2.0)] mols per 1 mol of the amino compound having a carboxyl group(s).

EXAMPLES

Now, the present invention will be described in further detail with reference to Examples. However, it should be understood that the present invention is by no means thereby restricted.

In Examples, HPLC means high performance liquid chromatography and NMR means nuclear magnetic resonance.

Further, measuring conditions for various measurements are as follows.

Measuring Condition for HPLC
Equipment used: SHIMADZU LC-10A series
Column used: INERTSIL ODS 2
Column temperature: 40° C.
Detection: UV 254 nm
Solvent composition: acetonitrile/20 mM phosphoric acid 80/20 (v/v)
Flow rate: 1.0 mL/min, or
Equipment used: SHIMADZU LC-10Avp
Column used: L-Column ODS
Column temperature: 40° C.
Detection: UV 233 nm
Solvent composition: acetonitrile/10 mM phosphoric acid buffer (pH 2.6) 35/65 (v/v) (containing 5 mM SDS (dodecyl sodium sulfate))
Flow rate: 1.0 mL/min A $^1$H-NMR spectrum was measured by using JNM-ECP300 and JNM-ECX300.

Further, DMSO-d6 means dimethylsulfoxide-d6 used for the solvent.

Example 1

4-Isothiocyanatobenzoic Acid

4-Aminobenzoic acid (5.00 g, 36.5 mmol) was added to a methylene chloride solution (51 mL) of thiocarbonyldiimidazole (8.45 g, 47.4 mmol) and triethylamine (5.6 mL, 40.2 mmol) at an internal temperature of at most 5° C., followed by stirring under cooling with ice for one hour. The mixture was dropped to a separately prepared mixed solution of concentrated hydrochloric acid (12.2 mL, 140.5 mmol) and n-heptane (51 mL) so that the internal temperature became from 25° C. to 30° C., whereupon a pale yellow suspension was obtained. This was stirred under cooling with ice for 3 hours, and the solid was collected by filtration and washed with water (50 mL) to obtain a pale yellow crude product. The obtained crude product was subjected to an operation of washing with water (50 mL) with stirring and collection by filtration twice, followed by drying under reduced pressure to obtain 4-isothiocyanatobenzoic acid as a pale yellow solid (6.23 g, yield: 95%, HPLC purity: 100.0%).

$^1$H-NMR (DMSO-d6) δ: 7.52 (d, J=8.7 Hz, 2H), 7.97 (d, J=8.7 Hz, 2H), 13.20 (brs, 1H).

Example 2

3-Isothiocyanatobenzoic Acid 3-aminobenzoic acid (5.00 g, 36.5 mmol) was added to a methylene chloride solution (51 mL) of thiocarbonyldiimidazole (7.8 g, 43.8 mmol) and triethylamine (5.6 mL, 40.2 mmol) at an internal temperature of at most 5° C., followed by stirring at −10° C. for one hour. The mixture was dropped to a separately prepared mixed solution of concentrated hydrochloric acid (11.6 mL, 133.0 mmol) and n-heptane (51 mL) as that the internal temperature became from 20° C. to 30° C., followed by stirring for one hour as it was. Then, the mixture was stirred under cooling with ice for 2 hours, and the obtained colorless solid was collected by filtration, washed with water (20 mL) four times and dried under reduced pressure to obtain 3-isothiocyanatobenzoic acid as a creamy solid (6.01 g, yield: 93%, HPLC purity: 99.8%).

$^1$H-NMR (DMSO-d6) δ: 7.58 (dd, J=8.1 Hz, 1H), 7.68 (ddd, J=1.2, 8.1 Hz, 1H), 7.86-7.92 (m, 2H), 13.34 (brs, 1H).

Example 3

4-Isothiocyanato-2-Chlorobenzoic Acid

A methylene chloride solution (235 mL) of triethylamine (30.6 mL, 219.5 mmol) and thiocarbonyldiimidazole (23.01 g, 129.14 mmol) was dropped to a methylene chloride solution (130 mL) of 4-amino-2-chlorobenzoic acid (18.84 g, 109.82 mmol) under cooling with ice, followed by stirring for one hour while an internal temperature of at most 10° C. was maintained. 4M hydrochloric acid (120 mL, 480 mmol) was dropped so that the internal temperature became at most 10° C., followed by stirring under cooling with ice for one hour. Water (10 mL) was added, and the formed pink solid was collected by filtration, washed with water (100 mL) five times and dried under reduced pressure to obtain 4-isothiocyanato-2-chlorobenzoic acid as a colorless solid (21.36 g, yield: 91%, HPLC purity: 98.2%).

$^1$H-NMR (DMSO-d6) δ: 7.19 (dd, J=2.1, 8.4 Hz, 1H), 7.35 (d, J=2.1 Hz, 1H), 8.03 (d, J=8.4 Hz, 1H).

Example 4

4-Isothiocyanato-2-Nitrobenzoic Acid

Triethylamine (55.8 µL, 0.4 mmol) and thiocarbonyldiimidazole (46.3 mg, 0.26 mmol) were added to a methylene chloride solution (0.4 mL) of 4-amino-2-nitrobenzoic acid (36.4 mg, 0.2 mmol) at room temperature, followed by stirring at room temperature for 10 minutes. The reaction mixture was dissolved in ethyl acetate and washed with 1 M hydrochloric acid, the organic layer was separated, and then the organic layer was dried over magnesium sulfate. Thereafter, filtration and concentration under reduced pressure to dryness were carried out to obtain 4-isothiocyanato-2-nitrobenzoic acid as a colorless solid (40 mg, yield: 89%, HPLC purity: 96.4%)

$^1$H-NMR (DMSO-d6) δ: 7.80 (dd, J=2.1, 8.1 Hz, 1H), 7.93 (d, J=8.1 Hz, 1H), 8.12 (d, J=2.1 Hz, 1H).

The structural formulae of the compounds synthesized in the above Examples are shown below. (Nos. represent example numbers.)

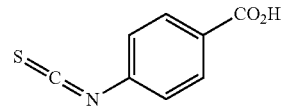
No. 1

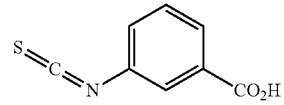
No. 2

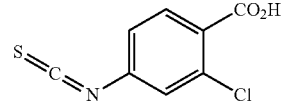
No. 3

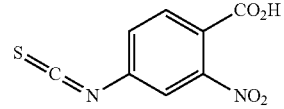
No. 4

INDUSTRIAL APPLICABILITY

According to the present invention, an isothiocyanate compound having a carboxyl group(s) useful as a product or a synthetic intermediate in the field of organic materials or drugs or agricultural chemicals, can be produced safely in a high yield and with high purity under mild conditions, and the production method of the present invention is useful as an industrial production method.

The invention claimed is:

1. A method for producing an isothiocyanate compound comprising a carboxyl group, the isothiocyanate compound represented by formula (2):

$$(SCN)_m\text{-A-B}\text{—}(CO_2H)_n \quad (2)$$

wherein m, n, A and B are, respectively, as defined for formula (1),
  the method comprising reacting (i) an amino compound comprising a carboxyl group, the amino compound represented by formula (1):

$$(H_2N)_m\text{-A-B}\text{—}(CO_2H)_n \quad (1)$$

wherein
  m and n, each are an integer of 1,
  A is a phenylene group that is unsubstituted or substituted with one or more halogen atoms or one or more nitro groups, and
  B is a single bond,
  with (ii) thiocarbonyldiimidazole in a solvent in the presence of a base; followed by treating with acid and at least one poor solvent selected from the group consisting of water, a $C_{5-8}$ alkane, diethyl ether and diisopropylether; then filtering said isothiocyanate compound.

2. The method of claim 1, wherein the base is a tertiary amine.

3. The method of claim 2, wherein the base is a tri $C_{1-6}$ alkylamine.

4. The method of claim 3, wherein the base is triethylamine.

5. The method of claim 1, wherein the solvent is a halogenated hydrocarbon.

6. The method of claim 5, wherein the solvent is methylene chloride.

7. The method of claim 1, wherein the acid is an acidic aqueous solution.

8. The method of claim 7, wherein the acidic aqueous solution is hydrochloric acid.

9. The method of claim 1, wherein the poor solvent is water or a $C_{5-8}$ alkane.

\* \* \* \* \*